(12) United States Patent
Burns

(10) Patent No.: US 7,093,302 B1
(45) Date of Patent: Aug. 22, 2006

(54) HELMET ASSEMBLY WITH ACCESSORY ATTACHMENT FEATURES

(76) Inventor: James A. Burns, 11140 20th Street Ct. N., Lake Elmo, MN (US) 55042

( * ) Notice: Subject to any disclaimer, the term of this patent is extended or adjusted under 35 U.S.C. 154(b) by 43 days.

(21) Appl. No.: 10/933,773

(22) Filed: Sep. 3, 2004

Related U.S. Application Data

(60) Provisional application No. 60/501,151, filed on Sep. 8, 2003.

(51) Int. Cl.
*A61F 9/06* (2006.01)

(52) U.S. Cl. .................................. 2/8.1; 2/9

(58) Field of Classification Search ............... 2/428, 2/468, 422, 6.2, 424, 5, 8, 9, 10, 171.3; 128/206.28, 128/206.24, 200.28, 201.22, 201.23, 201.24
See application file for complete search history.

(56) References Cited

U.S. PATENT DOCUMENTS

| | | | | |
|---|---|---|---|---|
| 2,371,712 | A * | 3/1945 | Scholl et al. ................... | 2/419 |
| 2,485,117 | A * | 10/1949 | Settle ................................ | 2/8 |
| 2,882,894 | A * | 4/1959 | Fahey et al. ........... | 128/201.23 |
| 2,926,357 | A * | 3/1960 | Edwards et al. ................... | 2/8 |
| 2,959,787 | A * | 11/1960 | McKirgan .......................... | 2/9 |
| 3,112,745 | A * | 12/1963 | Boyer .................... | 128/201.23 |
| 3,310,811 | A * | 3/1967 | Iacono, Jr. ....................... | 2/6.5 |
| 3,535,706 | A * | 10/1970 | Aileo ................................ | 2/5 |
| 3,881,198 | A * | 5/1975 | Waters ......................... | 2/171.3 |
| 4,035,845 | A * | 7/1977 | Hochwalt ........................ | 2/6.2 |
| 4,055,173 | A * | 10/1977 | Knab .......................... | 128/847 |
| 4,174,710 | A * | 11/1979 | Pampuch ............... | 128/206.24 |
| 4,207,882 | A * | 6/1980 | Lemere ................. | 128/206.15 |
| 4,495,657 | A * | 1/1985 | Bay ................................ | 2/10 |
| 4,744,107 | A * | 5/1988 | Fohl .............................. | 2/422 |
| 4,752,974 | A * | 6/1988 | Haino ............................ | 2/424 |
| 4,901,716 | A * | 2/1990 | Stackhouse et al. ... | 128/201.25 |
| 5,365,615 | A * | 11/1994 | Piszkin ........................... | 2/422 |
| 5,658,065 | A * | 8/1997 | Jamieson ...................... | 362/106 |
| 5,701,609 | A * | 12/1997 | Bridges .......................... | 2/422 |
| 5,742,937 | A * | 4/1998 | Baudou et al. .................. | 2/6.3 |
| 6,009,562 | A * | 1/2000 | Bullock et al. ................ | 2/422 |
| 6,016,805 | A * | 1/2000 | Burns et al. ........... | 128/206.24 |
| 6,826,783 | B1 * | 12/2004 | Grove et al. ..................... | 2/424 |
| 2005/0268907 | A1 * | 12/2005 | McFarlane ............. | 128/201.22 |

* cited by examiner

Primary Examiner—Rodney M. Lindsey
(74) Attorney, Agent, or Firm—Mark J. Burns

(57) ABSTRACT

A helmet assembly includes dedicated features that are configured to matingly engage with a mating structure attached to a distinct accessory unit. The corresponding mating configurations enable the operable securement of one or more of such distinct accessory units to the helmet body.

10 Claims, 4 Drawing Sheets

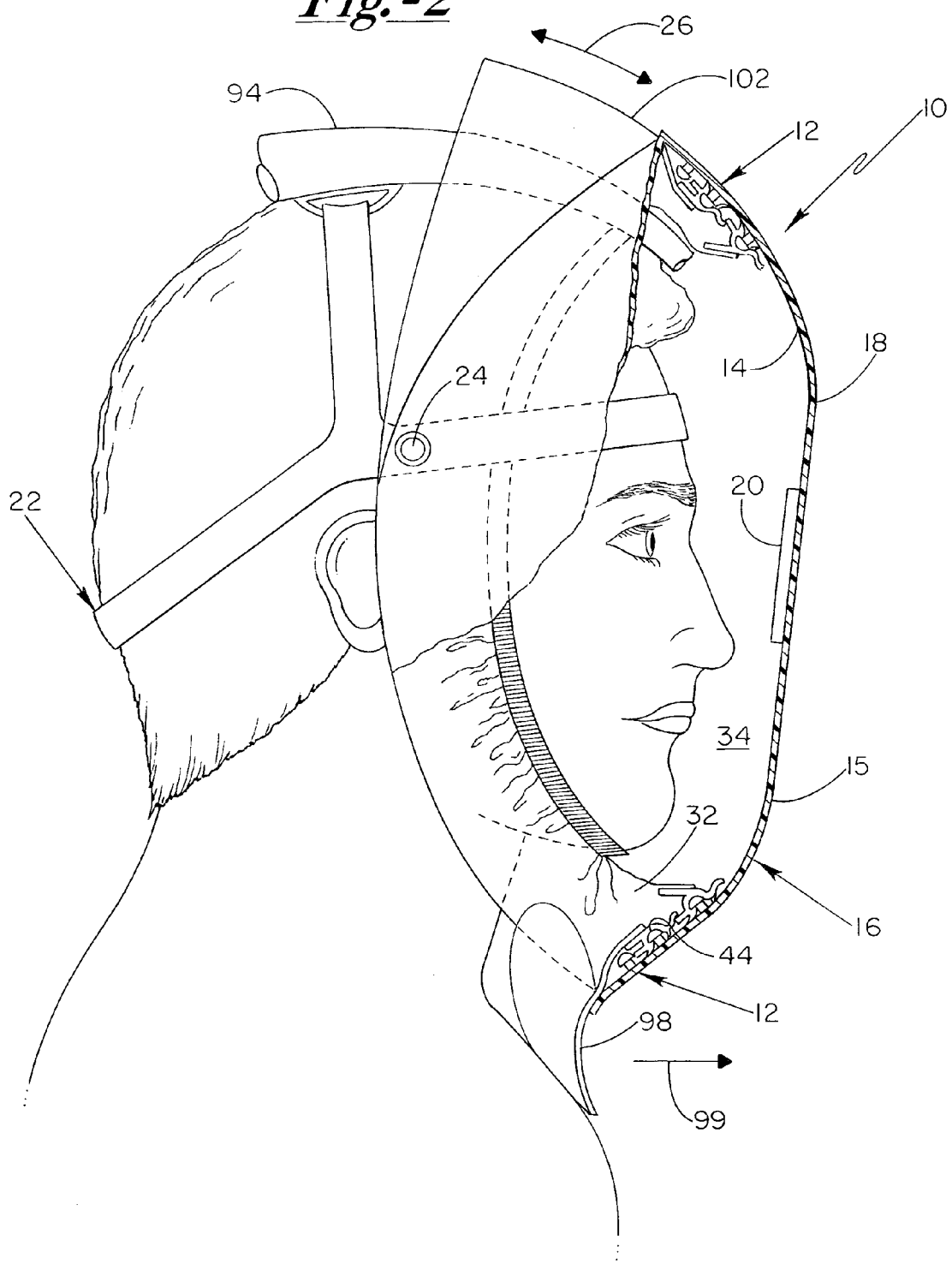

HELMET ASSEMBLY WITH ACCESSORY ATTACHMENT FEATURES

CROSS-REFERENCE TO RELATED APPLICATION

This application claims priority from U.S. Provisional Patent Application Ser. No. 60/501,151 filed on Sep. 8, 2003, the content of which is incorporated herein in its entirety.

FIELD OF THE INVENTION

This invention relates to protective welder's helmets, and in particular describes a synergistic method of construction utilizing peripheral attachment mechanisms on a welding helmet which facilitate a user-friendly and inexpensive method for affixing a face seal to the welding helmet so as to transform the helmet to an air supply system and/or allowing the helmet to be customized to provide improved comfort, protection, and convenience for a wide variety of welder physical features and/or specific job applications.

BACKGROUND OF THE INVENTION

It is well known that an extremely bright light which may contain a considerable amount of ultraviolet as well as infrared radiation is produced by typical welding operations. Extended exposure to such intense radiant energy may be very harmful to the welder's eye, and may cause radiant burning of the skin. In addition, sparks and heat from the welding process may cause localized conductive burning and discomfort. Thus, it is common practice for welders to make use of a helmet with a protective light filter arranged in front of the eyes, which helmet further offers protection from both radiant energy and localized burning and discomfort from sparks and heat. In addition, the welding operation may create toxic fumes, thus causing potential respiratory dangers. In these situations, the helmet my be attached to an air supply system that offers clean respiratory air, and in some instances conditioned air for added cooling or warming. To be effective, and to gain regulatory approval, the air supply system must incorporate a sealing system to the wearer's face, head, and in some cases neck to prevent contaminated air from entering the respiratory zone. This is not trivial, because the small air pressure within the breathing zone may drop to a negative pressure in certain time segments of the breathing cycle, depending on the size of the wearer, the level of exertion, etc. Thus, the sealing system must seal to a wide range of facial and head sizes comfortably, and also have a good sealing interface to the welding helmet. In addition, the sealing system must not impede the normal pivoting up and down procedure that many welders use to temporarily lift the helmet up for easy inspection of the work or setup, plus normal donning or removal from the head. Furthermore, this seal must be low in cost, preferably disposable, and easy to remove and replace as the sometimes hot, dirty conditions in which such helmets are used necessitates that the seal be changed frequently, sometimes daily, or even after each shift if the helmet has multiple users.

This invention provides a more economical, improved helmet sealing interface, and easier attachment method of the sealing system described above as compared to conventional methods.

In addition to a sealing system, this invention provides synergism by also offering novel helmet accessories which are also configured to operably engage with selected of the attachment means. Such helmet accessories provide increased protection to accommodate the range of physical features of the welders (e.g. long neck, long face, short neck, large head, large chest, etc.) or specific job applications such as, but not limited to, overhead welding, welding adjacent to another welder, welding while lying on back, or other confined situations.

Another example helmet accessory that may be selectively attached to welding helmets through the unique attachment mechanism of the present invention is a compact light device. Traditionally, welding helmets have employed vision windows that employ passive light filters having a sufficiently darkened shade to protect the user against the extremely bright light associated with the welding process. Typically, the shade utilized in such passive light filters is between 9 and 13. Due to the darkness of these passive light filters, the wearer must lift the helmet or remove the filter to clearly view objects in the line of vision. As such, the wearer is required to repeatedly lift and lower the helmet face shield throughout the work day in order to be able to visually inspect set-up, work progress, etc. More recently, auto-darkening filters have been incorporated into welding helmets in order to eliminate the need for the user to repeatedly lift and lower the helmet face shield. However, the "off" or least-tinted state of such auto-darkening filters is not fully transparent, but instead typically has a shade range of nearly 2 or 3, which represents the level of darkening commonly found in recreational sunglasses. In many cases, therefore, additional light is desired to better illuminate the field of vision external to the welding helmet such that the user need not lift and lower the face shield. A light device accessory that is selectively and removably securable to the helmet face shield accordingly provides an appropriate source of light for the wearer to selectively use.

An additional difficulty for wearers of welding helmets is in communicating while the helmet face shield is in the lowered position. To overcome this problem, a speaker system may be selectively secured to the welding helmet via the attachment mechanism of the present invention. Since the envisioned attachment mechanism preferably incorporates a plurality of distinct attachment features, a plurality of distinct helmet accessories may be utilized separately or simultaneously in combination with one another.

PRIOR ART

Conventional sealing shroud attachment is generally achieved by affixing adhesive-backed hook or loop strips (e.g. Velcro, Skotchmate, etc.) to interior surfaces of the weld shield, as shown in FIG. 1A, and then sewing a mating hook or loop strip unto the face sealing shroud, as shown attached in FIG. 1B. This system has many disadvantages: A) The hook and loop material is expensive. B) The welding helmets are generally molded in nylon, so as to enhance performance and weight characteristics. Other plastic materials may be utilized in the formation of such welding helmets, such as, for example, polyethylene or polypropylene. Many of such plastic materials, however, have relatively low surface energy, and therefore some surface preparation (such as, but not limited to electrical discharge) is required to develop a surface receptive to an adequate adhesive bond. Some recent adhesives claim adequate bonding to low energy surfaces, but these are typically quite expensive. C) A huge user cost penalty is incurred by requiring that the disposable face seals have mating hook and loop material sewn or attached to the fabric. D) The resultant hook and loop attachment of the fabric face seal to the interior of the weld shield is not leak proof—contaminated outside air can weave through the hook and loop interface and penetrate into the breathing chamber. E) The grasping capability of the hook/loop material on the helmet deteriorates with repeated removal cycles. F) The hook/loop material also accumulates dirt and debris over time, thereby lessening its mutual grasping ability. G) Mating engagement of the sealing shroud to the helmet using the hook/loop material is difficult to achieve without the aid of locating fixtures or proper training. H) Because the special plastic preparation technology is typically unavailable to the user, replacement hook/loop material does not adhere well to the now untreated plastic.

SUMMARY OF THE INVENTION

This invention utilizes a method of construction and design that provides peripheral attachment elements, used in conjunction with one or more relatively inexpensive mating structures attached to helmet accessories such as the face seal material to eliminate the above-described deficiencies of conventional systems. Additional details and advantages of the invention will become apparent in the description of the embodiments illustrated in the drawings. It is a primary object of the present invention to include the synergism of novel helmet attachments that provide additional protection, comfort, and convenience, and that interchangeably utilize either the very attachment elements which are operably engageable with the mating structures affixed to the face seal. In addition, the selective affixation method of the present invention may utilize a plurality of distinct attachment elements, such as adjacently disposed attachment elements in order to enable the operable securement of a plurality of helmet accessories to the helmet even simultaneously. Moreover, such distinct attachment elements may be simultaneously fabricated at little added expense.

Conventional helmet attachments consist of leather or other fabrics that are usually affixed to the welding helmet either by the afore described hook/loop methods or by fabric tie straps that manually wrap about several specifically spaced tabs or projections. These fabric or leather expanded coverage attachments ("extenders") engage or touch the skin and hair of the wearer, forcing the welder to either dispose of the relatively expensive items on a frequent basis, or to don a head or throat protector. Such an option is undesirable as re-used head or throat protectors are often times soaked in the previous days sweat, oil, and grime, and pockmarked with holes from the welding sparks.

Utilizing the construction method described in greater detail hereinbelow, this invention provides a method of attaching helmet accessories such as a face seal as well as an array of comfort, protection, and utility devices either separately or in conjunction with one another. Further, such accessories do not depend on the welder's face and head for support, but instead are registered and supported by the welding helmet. Such attachment devices are preferably made of easy to clean, reflective, durable material either identical or similar to the helmet material, that does not soak up sweat, oil, and grime, and is spark resistant.

BRIEF DESCRIPTION OF THE DRAWINGS

FIG. 2 is a partial cut-away side view of a helmet assembly of the present invention being worn by a user;

DETAILED DESCRIPTION OF THE PREFERRED EMBODIMENTS

Figure 1A:
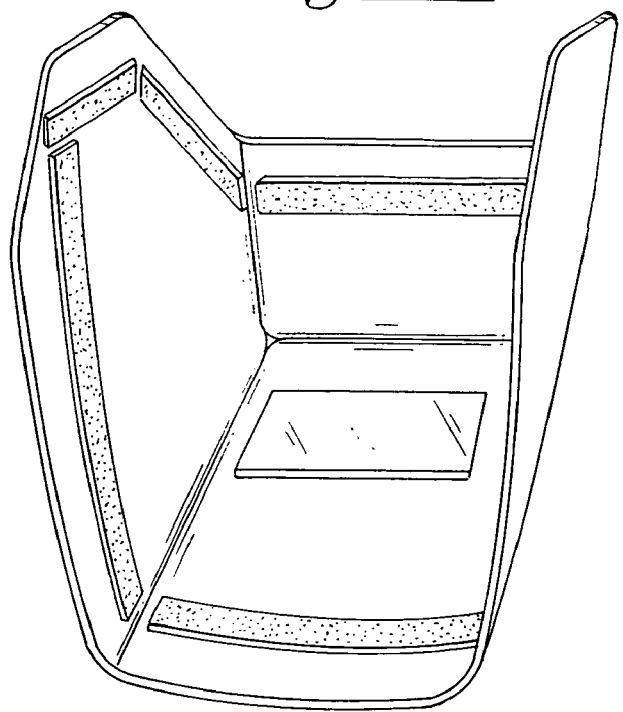
FIG. 1A is a rear plan view of a welder's helmet incorporating a conventional hook-and-loop material fixation mechanism.
Figure 1B:
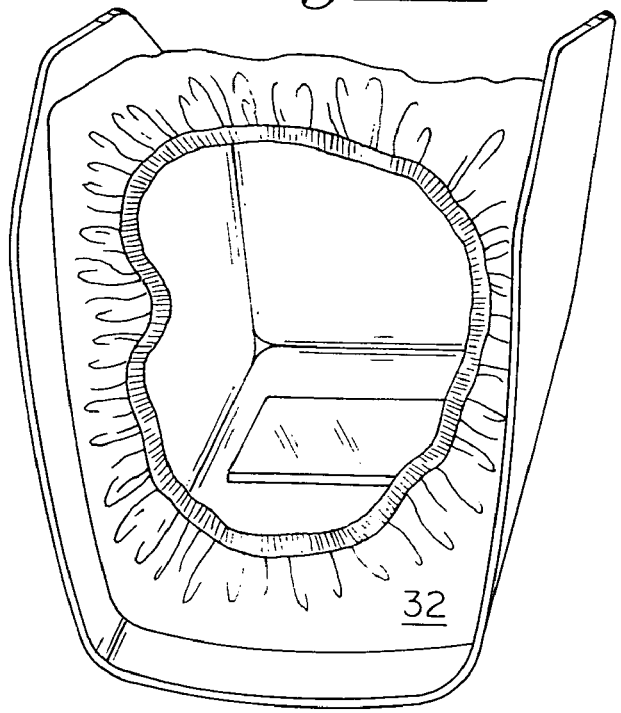
FIG. 1B is a rear plan view of the helmet of FIG. 1A including a face seal affixed thereto through the hook-and-loop material fixation mechanism.

The objects and advantages enumerated above together with other objects, features, and advances represented by the present invention will now be presented in terms of detailed embodiments described with reference to the attached drawing figures which are intended to be representative of various possible configurations of the invention. Other embodiments and aspects of the invention are recognized as being within the grasp of those having ordinary skill in the art.

With reference now to the drawing figures, and first to FIG. 2, a partial cut-away side view of a helmet assembly 10 of the present invention incorporating attachment means 12 disposed on an inner surface 14 of face shield 16. As shown in FIG. 2, face shield 16 is substantially conventional in its configuration, with a shield portion 18 having a vision window 20 disposed therein. Face shield 16 is preferably pivotally coupled to suspension 22 at pivot connection 24 thereof so as to provide for pivotal motion of face shield 16 about an axis defined by pivot connection 24 along a direction defined by arrow 26. Such suspension 22 and pivotal connection 24 are widely utilized in welder helmet assemblies and are well known in the art.

As indicated above, attachment means 12 are preferably disposed on inner surface 14 of face shield 16 so as to provide loci for removably or permanently securing one or more accessories to face shield 16 via one or more mating structures 38 disposed on such one or more accessories, and which one or more mating structures 38 are correspondingly configured to matingly engage with attachment means 12. As such, the present invention represents a universal attachment system utilizing an attachment means that operably mates or attaches with one or more specifically configured mating structures 38 that are selectively attached to a respective accessory that is desired to be operably secured to helmet assembly 10.

In a particular embodiment of the present invention, a face seal 32 is preferably operably secured about at least a portion of an inner periphery of face shield 16 for forming a relatively continuous barrier between a breathing zone 34 within the interior of helmet assembly 10 and the ambient environment external to helmet assembly 10. Breathing zone 34 is defined as the space generally between the user's face and inner surface 14 of face shield 16. Face seal 32 is preferably configured from a relatively compliant material such as fabric, synthetic rubbers, natural rubbers, and the like, so as to readily conform to users having disparate facial configurations, and to thereby assist in forming a generally continuous barrier about the user's face to fumes and other environmental conditions external to helmet assembly 10. In order to operably attach face seal 32 to the inner periphery of face shield 16, the present invention provides for one or more mating structures 38 secured to face seal 32 and matingly engageable to portion 12A of attachment means 12 disposed on inner surface 14 of face shield 16. An example of such an assembly is illustrated in the detailed side view of FIG. 3.

The above example illustrates the functionality of the attachment system of the present invention, whereby portion 12A of attachment means 12 is selectively and operably utilized to engage mating structure 38 that is attached to face seal 32, resulting in an easy and quick attachment therebetween, with good interface sealing between face seal 32 and inner surface 14 of face shield 16.

Although the above example describes the use of mating structure 38 with face seal 32, other accessories may incorporate a mating structure 38 of the present invention in order to be operably securable to face shield 16 at attachment means 12. The particular configuration for mating structures 38 associated with other accessories, however, may be modified as desired, so long as mating engagement with attachment means 12 is feasible. Several methods for affixation of mating structure 38 to accessories such as face seal 32 are contemplated by the present invention. Such methods include, for example, the use of sutures, adhesives, sonic welding, fasteners, as well as other attachment agents. In the embodiment illustrated in FIG. 3, mating structure 38 is sewn to face seal 32 via fabric sutures 39. To aid an attaching mating structure 38 to, for example, face seal 32, mating structure 38 may preferably include a fixation tab portion 40 extending outwardly from a receptacle portion 41 of mating structure 38, thereby providing a relatively easily accessible surface at which to effectuate connection between mating structure 38 and face seal 32.

Attachment means 12 preferably comprise a structure that is either integrally molded on interior surface 14 of face shield 16, or is formed as discrete attachment units that are separately secured to inner surface 14 of face shield 16 via adhesives, hook and loop type fasteners, screw fasteners, and the like. In the embodiment illustrated in FIGS. 2 and 3, attachment means 12 comprise one or more projections 44 integrally molded on inside surface 14 of face shield 16, with the projections each having a flange portion 46 extending radially outwardly therefrom, which flange portion 46 acts as a catch to operably engage a corresponding "notch" portion of mating structure 38. Such molded projections 44 form, for example, portions 12A, 12B, and 12C of attachment means 12 and are preferably located at substantially peripheral portions of inside surface 14 of face shield 16, so that face seal 32 may be selectively engaged thereat without interfering with the fit, comfort, or functionality of helmet assembly 10. Thus, face seal 32 is operably secured to face shield 16 via one or more distinct mating structures 38 which act as the operable interface therebetween.

Figure 3:
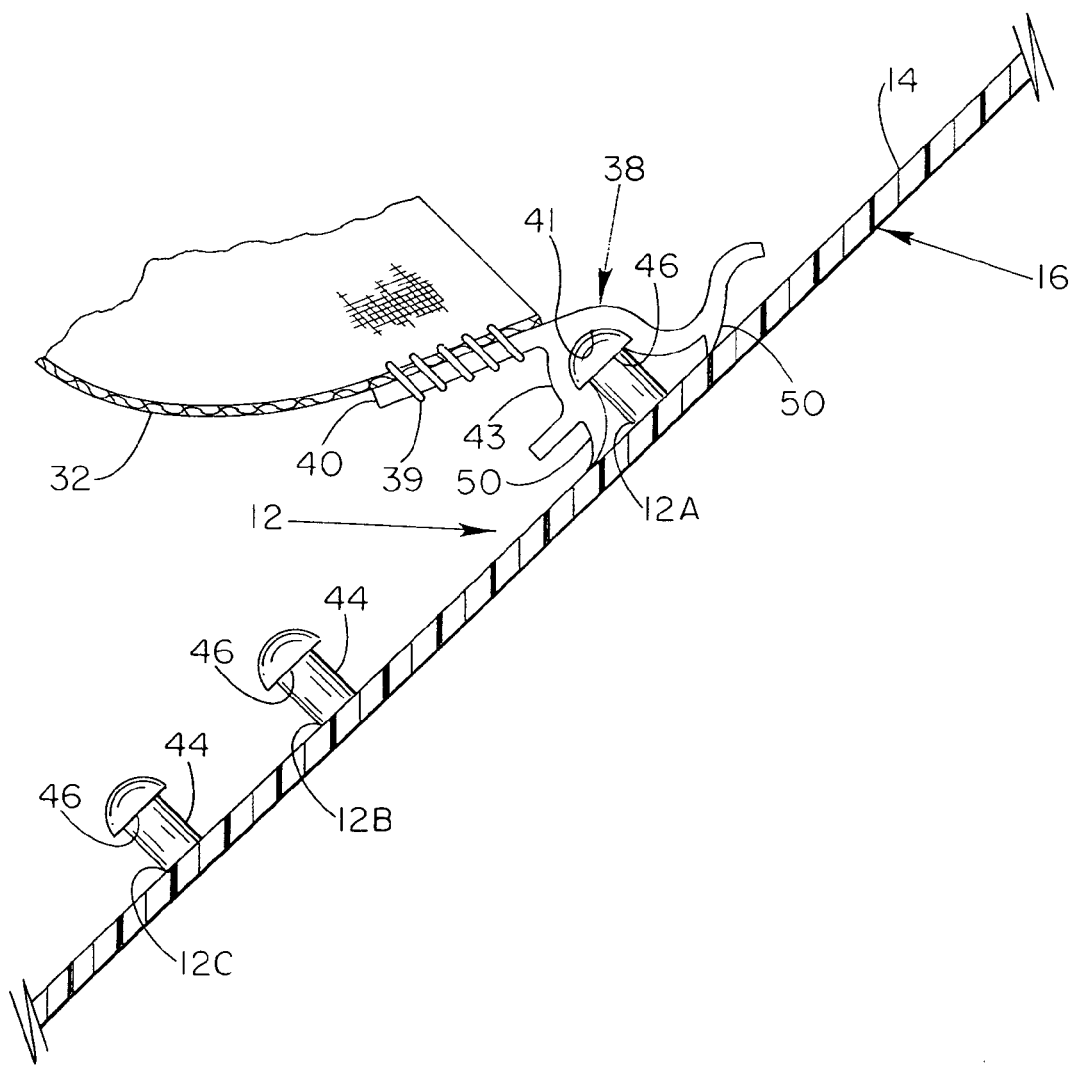
FIG. 3 is a cross-sectional side view of a portion of a helmet assembly of the present invention.

As best seen in the enlarged view of FIG. 3, mating structure 38 is preferably secured to face seal 32, as well as being configured for operable engagement with portion 12A of attachment means 12 that is connected to inside surface 14 of face shield 16. Mating structure 38 is preferably formed from a relatively resilient material, such that respective sides 43 of a receptacle portion 41 thereof may be "snap-fit" over and about the respective flange portions 46 of attachment portion 12A. In such a manner, a snug but removable engagement may selectively be established between respective pair of attachment portion 12A and mating structure 38.

As further shown in FIG. 3, mating structure 38 may preferably incorporate relatively flexible seal portions 50 which resiliently engage inner surface 14 of face shield 16 when mating structures 38 are coupled to attachment means 12. Accordingly, such seal portions 50 effectively inhibit infiltration of external gases into the breathing zone 34.

As described above, attachment means 12 preferably comprise a structure integrally molded on inner surface 14 of face shield 16. Attachment means 12 may therefore extend continuously about an entire periphery of face shield 16, or may instead be intermittently disposed thereat. In a particular intermittent embodiment of attachment means 12, one or more discrete sections of structure defining attachment means 12, each being between about 0.125 and about 2 inches in length, are disposed at predetermined portions of inner surface 14 of face shield 16. Such discrete sections may be either integrally molded with face shield 16, or may instead be distinct units separately affixed to face shield 16. Though attachment means 12 is preferably disposed at inner surface 14 of face shield 16, it is contemplated by the present invention to incorporate attachment means 12 at either or both of inner and/or outer surfaces 14, 15 of face shield 16, so that various accessories may be selectively secured to face shield 16, irrespective of its placement on an inner or outer surface of face shield 16. Moreover, such attachment means 12 may be located at positions other than peripheral regions of face shield 16, such as portions of face shield 16 within a perimeter region thereof.

Attachment means 12 of the present invention may be formed through a variety of methods such as, but not limited to, molding, heat or sonic forming, machining, cold staking, etc, which methods may be performed simultaneously with, or subsequently to, the formation of face shield 16. In other embodiments of the present invention, attachment means 12 may be separately affixed to face shield 16 by secondary operation.

The choice of methods by which to create attachment means 12 is to a large degree based on quantity, whereby fixed costs must be balanced against variable unit cost. Mating structure 38 is preferably fabricated from an inexpensive flexible plastic such as flexible PVC, urethanes, polyethylene, thermoplastic rubbers, and the like. The present invention contemplates a wide variety of configurations for attachment means 12 and mating structure 38, and is intended to be universal as to the specific shape and detail of the engaging elements. In addition, the method or technique of producing attachment means 12 and mating structure 38 is meant to be all-inclusive. A preferred embodiment of the present invention is to provide attachment means 12 on interior surface 14 of face shield 16 via a molding process if quantity allows, but does not exclude systems such as a separate piece or pieces being attached or formed, either to the interior or the outside of face shield 16. The molding technique itself is meant to be all-inclusive, with a variety of methods available for those skilled in the art. Individual mold pulls (either interior or exterior), collapsing cores, partial collapse, and sequenced cores are example methods embraced under this invention. The preferred embodiment of mating structure 38 attached to or part of face seal 32 is an extrusion part that is selectively attached to a fabric face seal 32.

Figure 4:
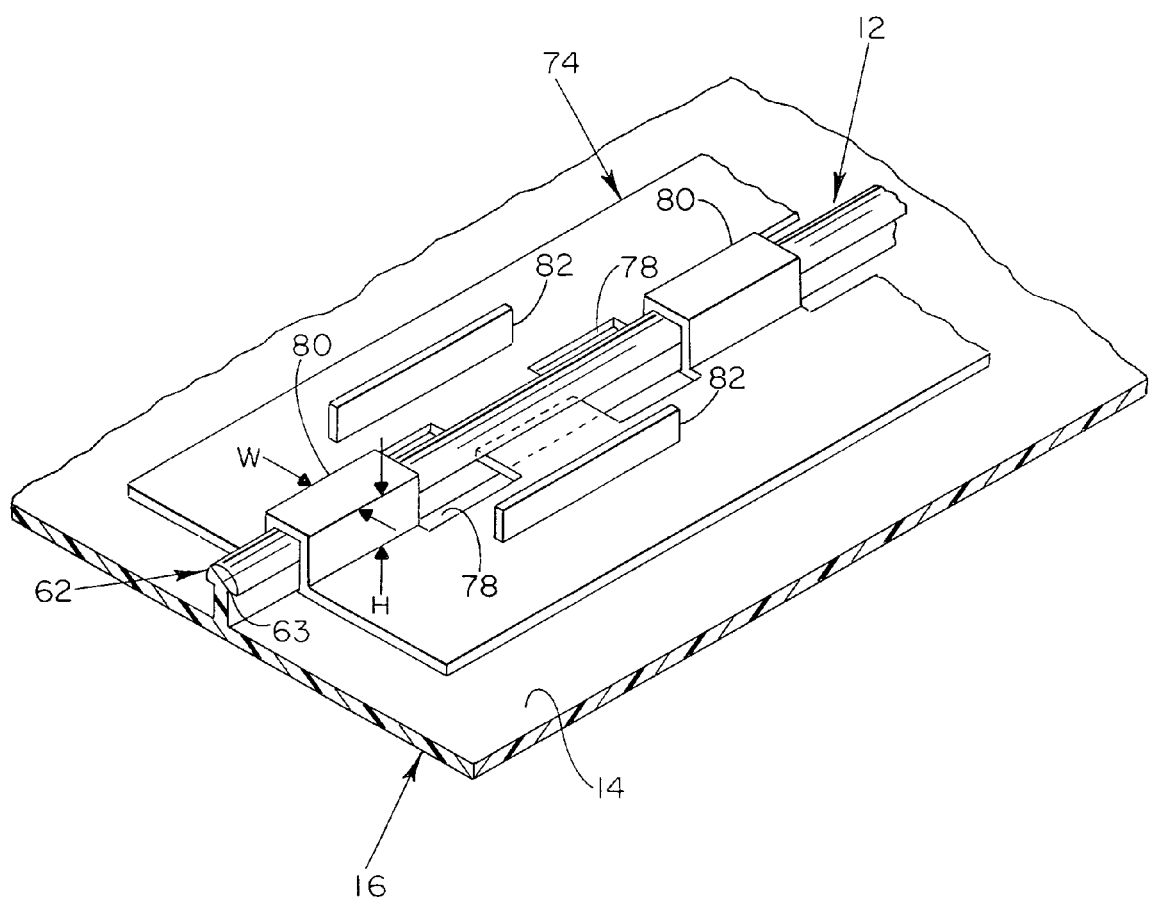
FIG. 4 is a perspective view of a portion of a helmet assembly of the present invention.

An exemplary embodiment of attachment means 12 is illustrated in FIG. 4, with a continuous or discontinuous rail 62 being provided on face shield 16 as an integrally formed or separately attached member serving as attachment means 12. A removably securable mating structure 74 for the helmet accessories is further illustrated in FIG. 4 as being complimentarily configured with attachment means 12 to selectively engage rail 62 thereof. Specifically, mating structure 74 includes a base portion 76 having an open channel 78 formed therein for operably and matingly engaging with rail 62 of attachment means 12. Clamp portions 80 may be integrally formed with base portion 76, and have a height "H" and a width "W" substantially equal to a corresponding height and width dimension of rail 62. Mating structure 74, and particularly clamp portions 80 thereof, is preferably fabricated from a relatively resilient material to thereby create a "snap-fit" over and about rail 62 of attachment means 12.

In embodiments wherein rail 62 is discontinuous, clamping portions 80 are not needed in order to secure mating structure 74 about rail 62. Instead, merely open channel 78 need be formed in base portion 76 with removal lugs 82 extending upwardly from base portion 76 at perimetorial sides of channel 78 in order to operably grasp rail 62 therebetween. Such removal lugs 82 may be incorporated whether or not rail 62 is continuous so as to provide for an access location to operably remove mating structure 74 from attachment means 12 via insertion of, for example, a blade screwdriver beneath a flange portion 63 of rail 62.

The embodiment illustrated in FIG. 2 includes an air supply system, which requires the use of face seal 32 and air plenum 94. In the arrangement of FIG. 2, plenum 94 is supported by suspension 22, and therefore face shield 16 moves with respect to plenum 94 when pivoted upward. To enable such relative movement, a sliding seal must be provided between face seal 32 and plenum 94, or, instead, sufficient face seal 32 material to allow the face shield 16 to pivot with respect to plenum 94 without breaching the barrier between breathing zone 34 and the environment external to helmet assembly 10.

In order to eliminate the drawbacks identified above, it is a preferred aspect of the present invention to support plenum 94 from face shield 16, again preferably utilizing the snap-on attachment means/mating structure combination of the present invention. Such a design eliminates the relative motion between plenum 94 and face seal 32.

As further illustrated in FIG. 2, a throat/neck protective accessory 98 is shown as being selectively engaged to attachment means 12, such as at attachment portions 12B, 12C. To do so, of course, mating structures 38 are preferably disposed on a surface of throat/neck protective accessory 98 that is in an operably facing relationship with inner surface 14 of face shield 16. In other embodiments, however, throat/neck protective accessory 98 may be selectively attachable to an attachment means 12 disposed on outer surface 15 of face shield 16. Preferably, throat/neck protective accessory 98 operably deflects outwardly along direction arrow 99 upon coming into contact with the user's body, as in when the user looks downwardly so as to move face shield 16 with respect to the relatively stationary torso. Moreover, throat/neck protective accessory 98 is preferably configured to operably rebound to an original configuration when removed from contact with, for example, the user's torso.

As is still further depicted in FIG. 2, a head protector accessory 102 is preferably operably attachable at attachment means 12 so as to provide an protection for the top of the user's head. In preferred embodiments, head protector accessory 102 is available to the user in a relatively large size that includes scribe lines, whereby the user can selectively cut away pre-designated portions of head protector accessory 102 to create a desired overall size thereof.

Other accessories that are selectively attachable to helmet assembly 10 are envisioned by the present invention, and may include, for example, side protectors, ear protectors, light devices, speakers, and the like. With the preferred configuration of attachment means 12, several of such accessories may be selectively secured to helmet assembly 10 so as to be simultaneously utilized by the user. Helmet assembly 10 of the present invention therefore, provides for a customizable apparatus that may selectively receive one or more accessory items, as is desired by the particular user.

The invention has been described herein in considerable detail in order to comply with the patent statutes, and to provide those skilled in the art with the information needed to apply the novel principles and to construct and use embodiments of the invention as required. However, it is to be understood that the invention can be carried out by specifically different devices and that various modifications can be accomplished without departing from the scope of the invention itself.

What is claimed is:

1. A helmet assembly being configured to operably secure one or more distinct accessory units thereto, said helmet assembly comprising:
   a helmet body;
   an attachment profile disposed on and extending inwardly from an inner surface of said helmet body; and
   a mating structure attached to each of said one or more accessory units, said mating structure being specifically configured to matingly engage with said attachment profile so as to provide for selective securement of said one or more accessory units to said helmet body, said mating structure including a sealing portion which sealingly engages with said inner surface of said helmet body when said mating structure is matingly engaged with said attachment profile.

2. A helmet assembly as in claim 1 wherein said attachment profile is configured to operably receive and simultaneously secure a plurality of said accessory units, each having a respective mating structure attached thereto.

3. A helmet assembly as in claim 1 wherein said helmet body is a welder's helmet.

4. A helmet assembly as in claim 3 wherein said one or more accessory units includes a face seal.

5. A helmet assembly as in claim 1 wherein said attachment profile is integrally formed with said helmet body.

6. A helmet assembly as in claim 5 wherein said attachment profile is molded with said helmet body in a one-step molding process.

7. A helmet assembly as in claim 1 wherein said attachment profile comprises at least one protrusion extending substantially about an inner periphery of said helmet body.

8. A helmet assembly as in claim 1 wherein said attachment profile comprises a plurality of protrusions extending substantially concentrically about an inner periphery of said helmet body.

9. A helmet assembly as in claim 1 wherein said attachment profile comprises a series of protrusions intermittently disposed adjacent to a periphery of said helmet body.

10. A method for selectively securing one or more distinct accessory units to a helmet body, comprising:
   (a) providing an attachment profile on an inner surface of said helmet body;
   (b) providing a mating structure on each of said one or more distinct accessory units, said mating structure being specifically configured to matingly engage with said attachment profile, said mating structure including a sealing portion which sealingly engages with said inner surface of said helmet body when said mating structure is matingly engaged with said attachment profile; and
   (c) placing said mating structure of respective ones of said accessory units in registration with said attachment profile.

* * * * *